(12) United States Patent
Ryan et al.

(10) Patent No.: US 7,803,130 B2
(45) Date of Patent: Sep. 28, 2010

(54) DEFLECTABLE TIP ACCESS SHEATH

(75) Inventors: Walter N. Ryan, Columbus, IN (US);
Tyler J. Bunch, Bloomington, IN (US);
Bruce J. DeMars, Bloomington, IN
(US); David A. Drewes, Jr.,
Bloomington, IN (US); **Gregory A.
Frankland**, Unionville, IN (US)

(73) Assignees: Vance Products Inc., Spencer, IN (US);
Sabin Corporation, Bloomington, IN
(US)

( * ) Notice: Subject to any disclaimer, the term of this
patent is extended or adjusted under 35
U.S.C. 154(b) by 618 days.

(21) Appl. No.: 11/649,683

(22) Filed: Jan. 4, 2007

(65) Prior Publication Data

US 2007/0203474 A1    Aug. 30, 2007

Related U.S. Application Data

(60) Provisional application No. 60/757,421, filed on Jan. 9, 2006.

(51) Int. Cl.
*A61M 31/00* (2006.01)
*A61M 37/00* (2006.01)
(52) U.S. Cl. ..................................... 604/95.04
(58) Field of Classification Search ............... 604/95.04, 604/95.05, 528–532, 533; 606/41
See application file for complete search history.

(56) References Cited

U.S. PATENT DOCUMENTS

| 4,997,424 | A | 3/1991 | Little |
| 5,188,606 | A | 2/1993 | Maloney et al. |
| RE34,502 | E | 1/1994 | Webster, Jr. |
| 5,304,142 | A | 4/1994 | Liebl et al. |
| 5,380,304 | A | 1/1995 | Parker |
| 5,429,616 | A | 7/1995 | Schaffer |
| 5,431,168 | A | 7/1995 | Webster, Jr. |

(Continued)

FOREIGN PATENT DOCUMENTS

EP    0 815 895 A1    1/1998

(Continued)

OTHER PUBLICATIONS

"Introducing the Next Generation of Ureteral Access Sheaths from Cook," Flexor Ureteral Access Sheath, copyright Cook Urological Inc. 2002, 4 pages.

(Continued)

*Primary Examiner*—Matthew F Desanto
(74) *Attorney, Agent, or Firm*—Brinks Hofer Gilson & Lione

(57) ABSTRACT

A disposable access sheath having a deflectable tip is provided. The access sheath is very flexible and allows a physician or other medical professional to provide diagnostic or therapeutic services to a remote body cavity. The access sheath has a deflectable tip that is able to bend at least 90° or 180° or more. This flexibility allows the physician or medical professional to make a very tight turn to visualize or treat the body cavity being treated. The access sheath may include a visualization system, a working channel, an irrigation channel, or other desirable features. The access sheath may include an interface at the proximal end of the working channel for insertion of an instrument for diagnosis or treatment of a human or mammalian patient.

26 Claims, 8 Drawing Sheets

U.S. PATENT DOCUMENTS

| | | | |
|---|---|---|---|
| 5,599,305 | A | 2/1997 | Hermann et al. |
| 5,700,253 | A | 12/1997 | Parker |
| 5,755,760 | A | 5/1998 | Maguire et al. |
| 5,843,031 | A | 12/1998 | Hermann et al. |
| 5,865,800 | A | 2/1999 | Mirarchi et al. |
| 5,897,529 | A | 4/1999 | Ponzi |
| 6,064,905 | A | 5/2000 | Webster, Jr. et al. |
| 6,066,125 | A | 5/2000 | Webster, Jr. |
| 6,066,126 | A | 5/2000 | Li et al. |
| 6,102,887 | A | 8/2000 | Altman |
| 6,123,699 | A | 9/2000 | Webster, Jr. |
| 6,183,463 | B1 | 2/2001 | Webster, Jr. |
| 6,198,974 | B1 | 3/2001 | Webster, Jr. |
| 6,203,507 | B1 | 3/2001 | Wadsworth et al. |
| 6,210,362 | B1 | 4/2001 | Ponzi |
| 6,210,407 | B1 | 4/2001 | Webster |
| 6,240,231 | B1 | 5/2001 | Ferrera et al. |
| 6,277,108 | B1 | 8/2001 | McBroom et al. |
| 6,319,244 | B2 | 11/2001 | Suresh et al. |
| 6,338,725 | B1 | 1/2002 | Hermann et al. |
| 6,346,099 | B1 | 2/2002 | Altman |
| 6,352,531 | B1 | 3/2002 | O'Connor et al. |
| 6,398,776 | B1 | 6/2002 | Sekino et al. |
| 6,419,641 | B1 | 7/2002 | Mark et al. |
| 6,458,076 | B1 | 10/2002 | Pruitt |
| 6,471,648 | B1 | 10/2002 | Gamelsky et al. |
| 6,475,184 | B1 | 11/2002 | Wang et al. |
| 6,500,167 | B1 * | 12/2002 | Webster, Jr. .................. 604/528 |
| 6,537,480 | B1 | 3/2003 | Becker et al. |
| 6,551,302 | B1 | 4/2003 | Rosinko et al. |
| 6,554,794 | B1 | 4/2003 | Mueller et al. |
| 6,571,131 | B1 | 5/2003 | Nguyen |
| 6,595,982 | B2 | 7/2003 | Sekino et al. |
| 6,613,017 | B1 | 9/2003 | Mickley |
| 6,641,564 | B1 | 11/2003 | Kraus |
| 6,712,789 | B1 | 3/2004 | Lange et al. |
| 6,716,223 | B2 | 4/2004 | Leopold et al. |
| 6,723,070 | B1 | 4/2004 | Arai et al. |
| 6,796,976 | B1 | 9/2004 | Chin et al. |
| 6,855,106 | B2 | 2/2005 | May et al. |
| 6,893,421 | B1 | 5/2005 | Larson et al. |
| 6,951,555 | B1 | 10/2005 | Suresh et al. |
| 7,122,020 | B2 * | 10/2006 | Mogul ..................... 604/95.04 |
| 7,135,015 | B2 | 11/2006 | Dulak et al. |
| 2001/0034514 | A1 | 10/2001 | Parker |
| 2001/0037084 | A1 | 11/2001 | Nardeo |
| 2002/0115983 | A1 * | 8/2002 | Sekino et al. ............... 604/528 |
| 2002/0161353 | A1 | 10/2002 | Kortelling |
| 2003/0004460 | A1 * | 1/2003 | Bedell ..................... 604/95.04 |
| 2003/0135156 | A1 | 7/2003 | Bencini et al. |
| 2003/0135198 | A1 | 7/2003 | Berhow et al. |
| 2003/0236493 | A1 | 12/2003 | Mauch |
| 2004/0015138 | A1 | 1/2004 | Currier et al. |
| 2004/0044350 | A1 | 3/2004 | Martin et al. |
| 2004/0054377 | A1 | 3/2004 | Foster et al. |
| 2004/0092962 | A1 | 5/2004 | Thornton et al. |
| 2004/0176744 | A1 | 9/2004 | Lange et al. |
| 2004/0193112 | A1 | 9/2004 | Glazier et al. |
| 2004/0220549 | A1 | 11/2004 | Dittman et al. |
| 2004/0236346 | A1 | 11/2004 | Parker |
| 2005/0004515 | A1 | 1/2005 | Hart et al. |
| 2005/0065467 | A1 | 3/2005 | Pudelko et al. |
| 2005/0065474 | A1 | 3/2005 | Larson et al. |
| 2005/0165366 | A1 | 7/2005 | Brustad et al. |
| 2005/0192606 | A1 | 9/2005 | Paul, Jr. et al. |
| 2005/0222581 | A1 | 10/2005 | Fischer, Jr. et al. |
| 2005/0222664 | A1 | 10/2005 | Parker |
| 2005/0228479 | A1 | 10/2005 | Pavcnik et al. |
| 2005/0256452 | A1 * | 11/2005 | DeMarchi et al. ......... 604/95.04 |
| 2007/0078455 | A1 * | 4/2007 | Rashidi ....................... 606/41 |

FOREIGN PATENT DOCUMENTS

| | | |
|---|---|---|
| EP | 1 484 003 A1 | 12/2004 |
| WO | WO 91/01772 | 2/1991 |
| WO | WO 02/11807 A2 | 2/2002 |
| WO | WO 03/090835 A1 | 11/2003 |
| WO | WO 2004/096015 A2 | 11/2004 |
| WO | WO 2004/103434 A2 | 12/2004 |
| WO | WO 2005/072806 A2 | 8/2005 |
| WO | WO 2005/123169 A1 | 12/2005 |

OTHER PUBLICATIONS

"The Polyscope," from http://www.matricsmedical.com/PRODUCTS/index_solution.html, Matrics Medical, printed Nov. 11, 2005, 4 pages.

International Preliminary Report on Patentability for related PCT application No. PCT/US2007/000073 dated Jul. 24, 2008.

International Search Report from PCT International application No. PCT/US2007/000073 dated Aug. 20, 2007 (6 pages).

* cited by examiner

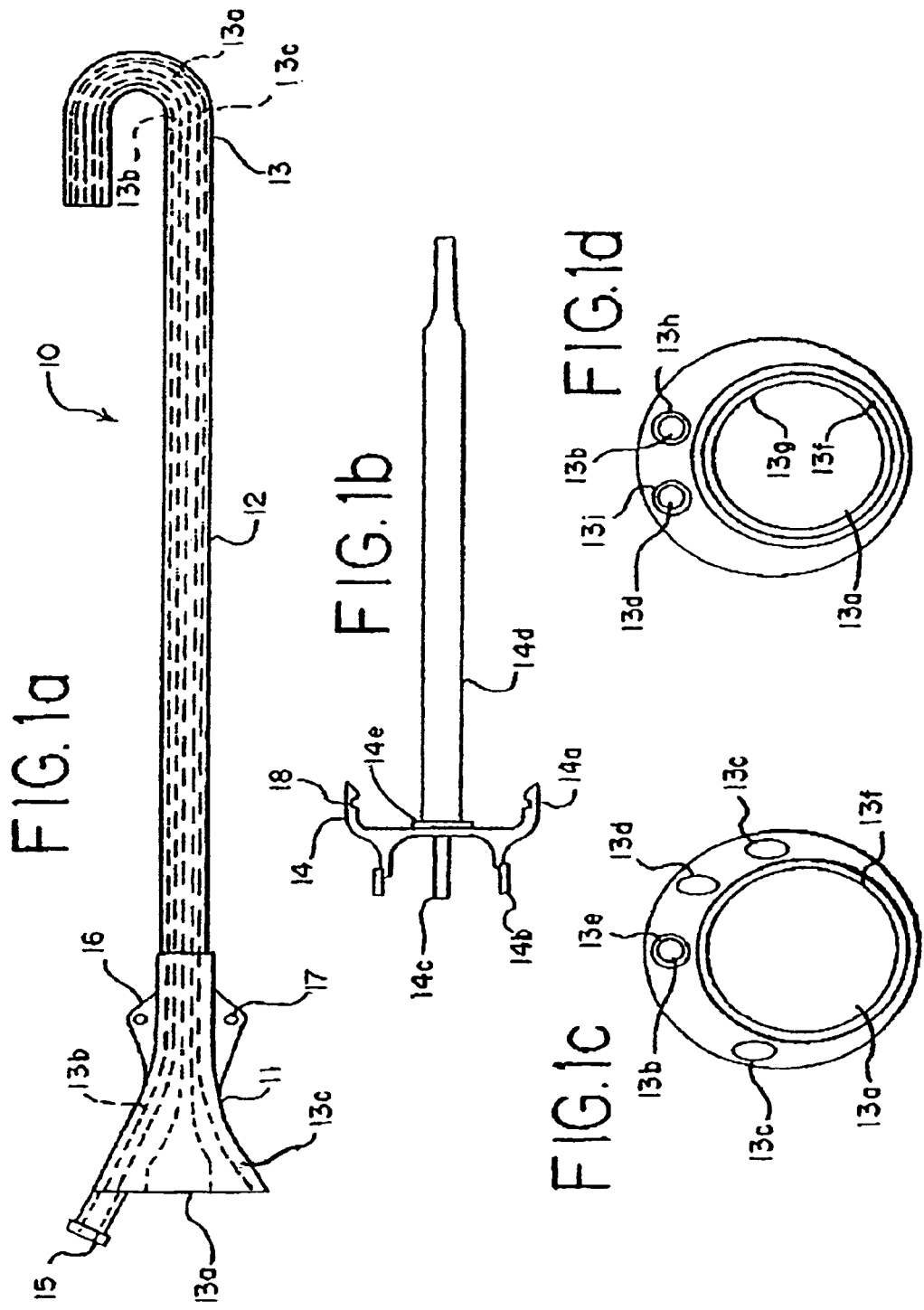

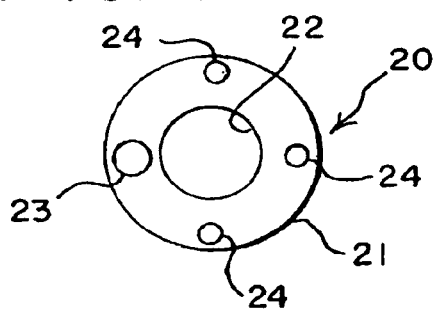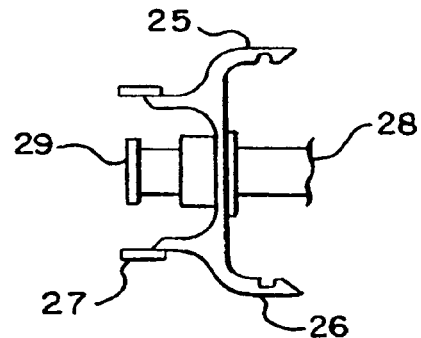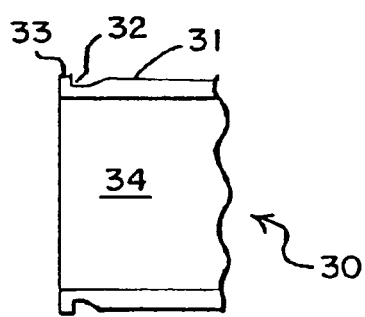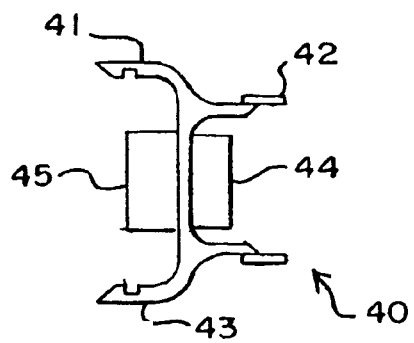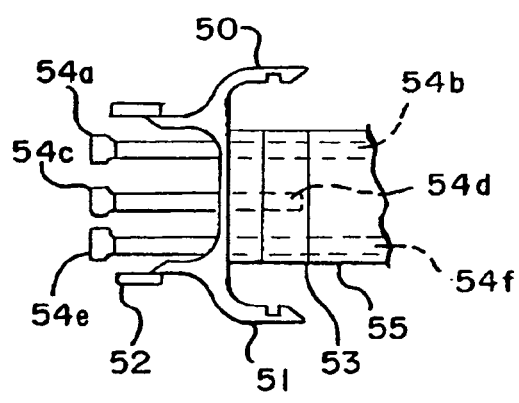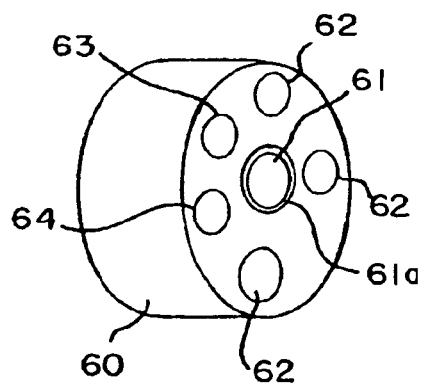

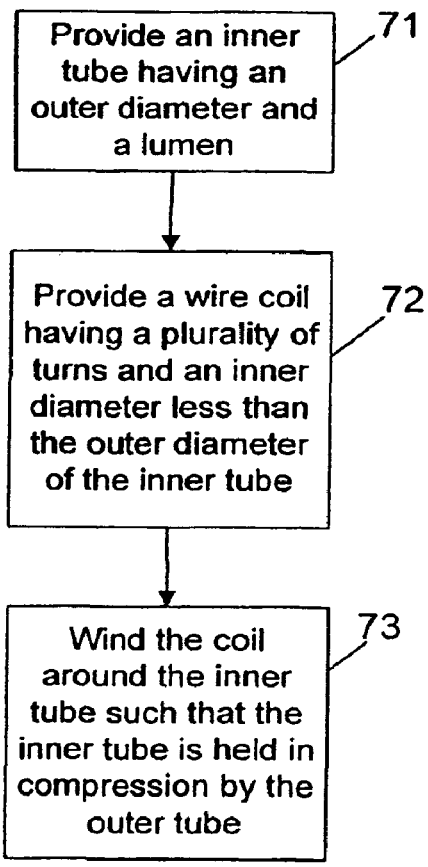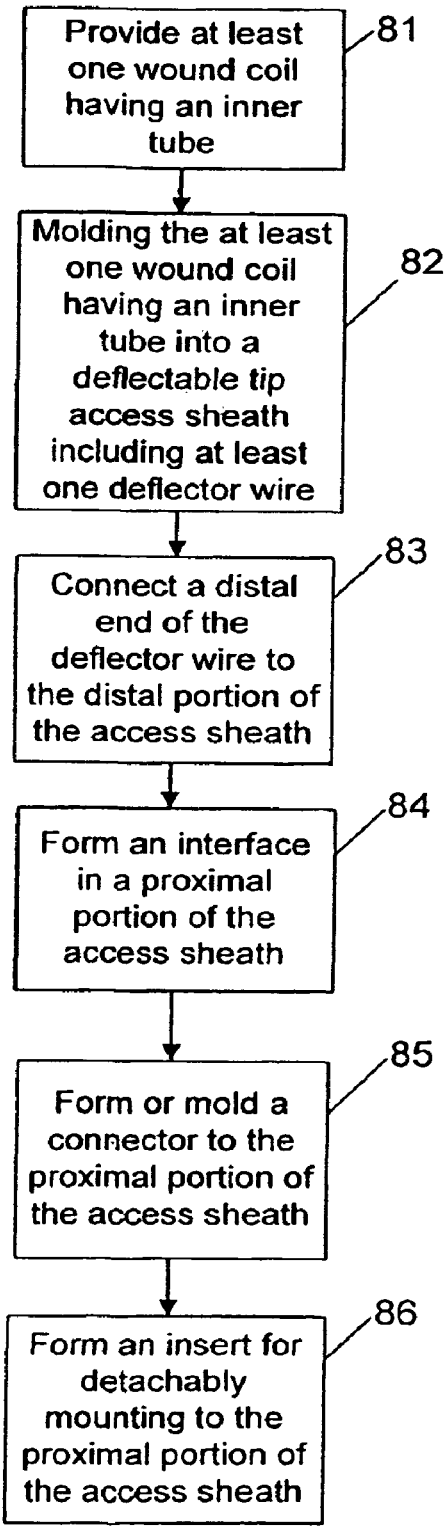

DEFLECTABLE TIP ACCESS SHEATH

RELATED APPLICATIONS

The present patent document claims the benefit of the filing date under 35 U.S.C. §119(e) of Provisional U.S. Patent Application Ser. No. 60/757,421, filed Jan. 9, 2006, which is hereby incorporated by reference in its entirety.

TECHNICAL FIELD

This device relates to the field of endoscopic and laparoscopic medical devices, primarily useful in minimally-invasive surgery.

BACKGROUND

Access sheaths, such as ureteral access sheaths, may be used to gain access to body cavities and lumens during endoscopic and laparoscopic surgery, and by other procedures that generally use minimally invasive techniques. Thus, a ureteral access sheath may be used with an endoscope for finding and removing kidney stones, and may also be used in other applications, such as for access to bile ducts. Other applications for which an access sheath has been used include vascular procedures, as well as procedures requiring gastro-intestinal access, uterine access, and bronchial access. Thus, sheaths may be used in combination with endoscopes, hysteroscopes, sigmoidoscopes, bronchoscopes, and many other types of instruments meant for minimally-invasive techniques.

Using a sheath provides for a way to protect the tissues of a patient during a procedure. For instance, if a kidney stone is to be removed, a retrieval basket may require many passages back and forth across a patient's ureter to remove stone fragments. A wire basket or other device is first passed through the ureter to retrieve stone fragments, and then passes back through to remove the captured fragments. Passing the basket through an access sheath instead of the ureter itself avoids trauma to the ureter and surrounding tissues.

One problem that is common to all procedures in which these devices are used is that more and more is expected from the surgeon and operating team. For instance, now that an access sheath may be used for access across a ureter, the surgeon may wish to use the sheath for access not only for an endoscope, but also for multiple endoscopic instruments, such as a retrieval basket, a stone "blocker" or backstop, a fiberoptic laser to break up stones, a safety wire, an operating wire, or a system to provide irrigation or to instill contrast agents. While all these systems are desirable, it is difficult to operate them all at the same time and through the same access sheath. Thus, the surgeon may instead use an endoscope.

Removal of kidney stones and other calculi within body cavities may be accomplished with an endoscope or other expensive piece of equipment. An endoscope is inserted into the patient, desirably using a body passageway, such as a urethra, a ureter, or a blood vessel. The endoscope includes an optical system, a working channel, and a way to maneuver the endoscope so that the surgeon can accomplish a therapeutic or diagnostic procedure. The surgeon positions the endoscope so that the surgeon can observe the desired body part of the patient using the optical system, with irrigation if necessary. The surgeon then uses at least one instrument, such as a laser fiber or a grasper, to break up and remove objects from the body passageway. The endoscope may also be used for diagnostic purposes, such as for observing the desired portion of the patient and then taking a biopsy sample.

Flexible endoscopes are very expensive pieces of equipment. When this application refers to endoscopes, primarily flexible endoscopes are intended. They may cost from $10,000 to $20,00, and are typically used for no more than 10-15 procedures before they require a $3000-$5000 overhaul. Part of the problem may be the very extensive cleaning and sterilization that is required after each patient. After the overhaul, the endoscope may typically be serviceable for only another 10 procedures before requiring additional overhaul. Thus, endoscopes are very expensive and they require great attention and maintenance. Because damage is not always apparent to hospital personnel, the need for repair or an overhaul may become obvious during a medical procedure, causing a delay in completing the procedure. In addition, multiple endoscopes must be kept in stock to assure their availability at all times.

What is needed is a better way to access body cavities during endoscopic and laparoscopic surgery. Highly desirable would be an access sheath with greater capabilities, the sheath adaptable for use in a variety of procedures, while still allowing important access functions. What is needed is an access sheath that allows the surgeon to best use valuable space in the sheath or other minimally-invasive device used on the patient. What is needed is a way to better use the space available to a surgeon with an access sheath.

BRIEF SUMMARY

One embodiment of the invention is a deflectable tip access sheath. The sheath includes a proximal portion with at least one interface, a distal portion adapted for bending at an angle and an elongated portion extending from the proximal portion through the distal portion the elongated portion including a working lumen and two additional lumens, one of the lumens adapted to receive an optical system. The sheath also includes at least one deflector filament in at least one of said additional lumens, the at least one deflector filament operatively coupled to the distal portion and extending to the proximal portion.

Another embodiment is a deflectable tip access sheath. The deflectable tip access sheath includes an elongated access sheath extending from a proximal portion to a distal portion, the proximal portion having at least one connector and an interface, at least one coil embedded within the access sheath, the coil reinforcing at least a portion of a lumen extending from the proximal portion to the distal portion, and at least one additional lumen extending from the proximal portion to the distal portion and adapted to receive an optical system or a portion of an irrigation system. The access sheath also includes at least one deflector filament operatively coupled to the distal portion and extending through the access sheath. The deflector wire and access sheath are adapted for bending the distal portion of the access sheath at an angle.

Another embodiment is a method of making a deflectable tip access sheath. The method includes forming a reinforced lumen by encapsulating a wire coil having a plurality of turns into a deflectable tip access sheath having a proximal portion and a distal portion, and forming at least one additional lumen extending from the proximal portion to the distal portion, the at least one additional lumen adapted to receive an optical system or a portion of an irrigation system.

The method also includes providing at least one deflector filament and operatively coupling a distal end of the deflector filament to the distal portion of the access sheath and extending a proximal end of the at least one deflector filament to the proximal portion of the access sheath, wherein tensioning of the at least one deflector filament enables the distal portion of the access sheath to bend at an angle.

There are many aspects and embodiments of the invention, of which the following are intended to be illustrative rather than limiting.

BRIEF DESCRIPTION OF THE DRAWINGS

The embodiments will be further described in connection with the attached drawing figures. It is intended that the drawings included as a part of this specification be illustrative of the embodiments and should in no way be considered as a limitation on the scope of the invention.

FIG. 1a is a side view of a first embodiment of a deflectable tip access sheath;

FIG. 1b is a side view of an insert for use with the embodiment of FIG. 1a;

FIG. 1c is a cross-sectional view of an additional embodiment of a deflectable tip access sheath;

FIG. 1d is a cross-sectional view of another embodiment;

FIG. 2 is a cross-sectional view of another embodiment of a deflectable tip access sheath;

FIG. 3a is a side view of another insert embodiment;

FIG. 3b is a partial cross-sectional view of an insert;

FIG. 4 is a side view of another insert embodiment;

FIG. 5 is a side view of an additional insert embodiment;

FIG. 6 is a perspective partial cross-sectional view of another embodiment of a deflectable tip access sheath;

FIGS. 7 and 8 are flow charts for methods of making deflectable tip access sheaths;

DETAILED DESCRIPTION OF THE DRAWINGS AND THE PRESENTLY PREFERRED EMBODIMENTS

Figure 9:
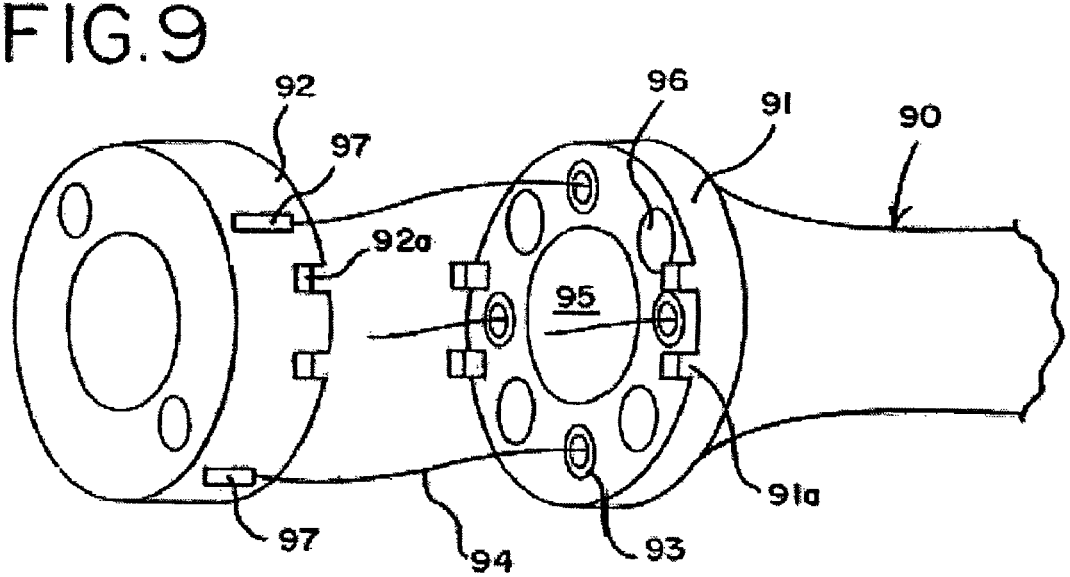
FIGS. 9 and 10 depict a handle suitable for controlling the sheath tip.

Embodiments of the present invention concern an access sheath, typically used for endoscopic or laparoscopic surgical procedures. The differences between an access sheath and an endoscope are subtle. An endoscope, especially a flexible endoscope, is an optical instrument that transmits light and carries images back to an observer through a flexible bundle of small (about 10 μm) transparent fibers. Such an endoscope is used to inspect interior portions of the body, may be equipped with mechanisms for steering, and may have additional lumens for allowing sampling and/or operative instruments along their axis to the internal site. Stedman's Medical Dictionary, 27th ed. at 594 (2000). The chief distinguishing feature of a steerable access sheath is the absence of an integral lighting device.

Thus, an endoscope first and foremost is a medical device for diagnostic procedures, and is defined as an optical instrument. The instrument may or may not have steering mechanisms, and may or may not have an additional lumen, i.e., a working channel, for sampling or operating instruments. Endoscopes are typically narrow, with an outer diameter from about 3.0 to 5.6 or 6 mm outer diameter. In urology, the "working channel" may be from about 0.8 to 1.2 mm in diameter (about 2.4 Fr. to 3.6 Fr.). In contrast, many access sheaths currently sold have a working channel with a minimum of about 9.5 Fr. up to 14 Fr., with an outer diameter from about 11 Fr. (3.7 mm) to about 16 Fr. (5.4 mm). An access sheath is not primarily an optical instrument and does not have an integral optical system.

One embodiment of a deflectable tip access sheath has a first, large lumen and a single second smaller lumen. Such an embodiment is depicted in FIG. 1a. Deflectable tip access sheath 10 includes a proximal portion 11, an elongated portion 12, and a distal portion 13. The access sheath includes a first lumen 13a and a smaller second lumen 13b. Both lumens extend from the proximal portion to the distal portion. First lumen 13a desirably is lined on its inner surface with a lubricious polymer, such as fluoropolymer liner, such as PTFE or Teflon®. Second lumen 13b is also desirably lined with a fluoropolymer or other lubricious coating on its inner surface. Polyethylene, polypropylene or other polymer may be used instead.

First lumen 13a is desirable larger and may act as a working lumen if the access sheath will be used for therapeutic or diagnostic purposes, such as removing kidney or bile stones, or retrieving a biopsy sample. In these instances, second lumen 13b may be used for an optical system to guide the physician or medical professional providing the therapeutic service. The optical system may be connected by a connector 15 on the proximal portion of the access sheath. There may be additional lumens for an irrigation system to aid the optical system, or the first lumen 13a may be used for the irrigation system.

The deflectable tip access sheath includes at least one deflector filament or wire 13c connected at its distal end to the distal portion of the access sheath. The deflector wire is preferably provided within a lumen within access sheath 10 so that the tip of the access sheath may easily be bent and maneuvered by the surgeon. The lumen or lumens for the deflector wires may not extend through to the distal end of the access sheath, but may terminate close to the distal end. The distal end of the deflector wire is anchored within the sheath, so that when tension is applied to the wire, the wire will cause the tip to deflect. The proximal end of the deflector wire may be joined to a thumb actuator as shown, for example, in FIGS. 12-14. Alternatively, the access sheath may be provided with its own integral handle for manipulation of the deflector filament or wire. Each wire or filament may be a single steel wire, or may be wire bundle. Alternatively, the access sheath may use filaments made from other materials, such as nylons, polyesters, or other polymers, or polymers reinforced with glass, carbon, or metallic wires or fibers.

Alternatively, the access sheath may include more than one deflector wire or filament, preferably distributed radially across the distal and proximal ends of the access sheath. For instance, the deflector wires or filaments may be connected at intervals of 180°, 120°, or 90°, if there are, respectively, 2, 3, or 4 wires. The deflectable tip access sheath is preferably sufficiently flexible that the tip, the end 1-3 cm, may be bent around at an angle of at least 90°. In other embodiments, the tip may be bent around at an angle of at least 180° or more, such as 225-270°.

The liners described above make the inner surface smooth and lubricious, easing the passage of devices or fluids through the lumen. The access sheath itself may be made from a polymeric material, such as silicone, nylon, or urethane. Any medically acceptable thermoplastic or thermoset material may be used, including PTFE, a fluoropolymer, polyethylene, polypropylene, acetal, urethane, and others. In some embodiments, the second lumen may not have a lining and may instead be defined merely as a lumen of relatively constant diameter that remains when a plug or mandrel is removed after the material in the elongated section is formed or consolidated.

The deflectable tip access sheath may include an insert, as depicted in FIG. 1b. Insert 14 is meant to clip onto the proximal portion of the deflectable tip access sheath, using interface 14a and a mating proximal portion 11 of access sheath 10, as shown in FIG. 3b. Interface 14a is operated by finger-levers 14b, the operator squeezing the levers to part interface portions 14a in order to apply interface 14 to the access sheath. The operator then releases the levers, allowing the interface portions 14a and notches 18 to latch to the proximal portion of the access sheath.

Interface 14 may include control portion 14c and may also include diagnostic or therapeutic device 14d. Control portion 14c may be a proximal portion of a sheath or a control rod, or other connection for a desired diagnostic or therapeutic device. The control portion 14c would be used to extend a control rod for a retrieval basket, or to retract a sheath used with a retrieval basket.

Device 14d may be a diagnostic or therapeutic device, such as a retriever for kidney stones. The device may include an outer sheath (as shown) and an inner portion, such as a basket retriever, whose control rod may be control portion 14c. Alternatively, the device may include a laser fiber for breaking up calculi in a kidney or other body organ, so that the particles may then be retrieved and removed through the deflectable tip access sheath. Device 14d may include a seal 14e for sealing against a mating interface on the access sheath, or may fit more loosely, as appropriate.

Additional embodiments of deflectable-tip access sheaths are depicted in FIGS. 1c and 1d. In FIG. 1c, the cross section of an access sheath includes main lumen 13a, formed on the inside of coiled wire 13f. In this embodiment, lumen 13b is lined with a polymeric or plastic liner 13e. There are two lumens 13c, at about 180°, for deflector wires. There is an additional lumen 13d. If lumen 13b is used for an optical system, lumen 13d may be suitable for an irrigation system. If the optical system includes its own irrigation system, lumen 13d may be suitable for removal of fluid from the operational theater.

An optical system may be removably assembled into one of the lumens of the deflectable tip access sheath. These components preferably include a lens on the distal portion of the access sheath, and optical fibers for transmitting light to the lens and transmitting images from the lens to a user. An eyepiece and a light source are also desirable components but may or may not be part of a removable optical assembly. Components for an optical system may be purchased, for example, from Fujikura America, Atlanta, Ga. These include image fibers, light sources and light guides, and fiberscopes with image fibers, eyepieces, and lenses. These components may be integrated into a very thin, useful, and inexpensive access sheath having a deflectable tip. The access sheath is desirably sufficiently inexpensive for one-time only use.

A cross-section of another embodiment is depicted in FIG. 1d. In this embodiment, main lumen 13a is formed within wound coil 13f and inner polymeric liner 13g. As described below, the coil is tightly wound around the polymeric liner in such a way as to keep the liner in compression. In this embodiment, lumen 13b also has a liner 13h, such as a plastic liner, and lumen 13d has a liner 13b. Lumens 13b and 13d may be used for the diagnostic or therapeutic purposes described above. Alternatively, the lumens may be much smaller and may be used for the wires used to deflect the tips of the access sheath.

Referring to FIG. 1a, proximal portion 11 includes optional handles or ribs 16. Two ribs are shown at 180° on the proximal portion. The ribs are thin projections from the proximal portion and are meant to help a user orient and grasp the sheath. For instance, a user may place the ribs between joints of a user's adjacent fingers to grasp and steady the access sheath. The ribs may also have one or more optional bores 17. Bore 17 allows a user to use a pin or string to attach to a surgical drape.

As mentioned above, one embodiment of the invention includes a connector 15, such as a Luer lock connector, for one of the lumens in the sheath. The connector may be suitable for a fluid connection, such as for providing irrigation to or drainage from the operating site. Other embodiments may use different connectors for the lumens, such as for connecting to an optical system. Other interfaces for the lumens may include traditional connectors meant for use with a mating connector, or may include a septum or a sealing surface meant for use with another sealing surface.

Figure 11:
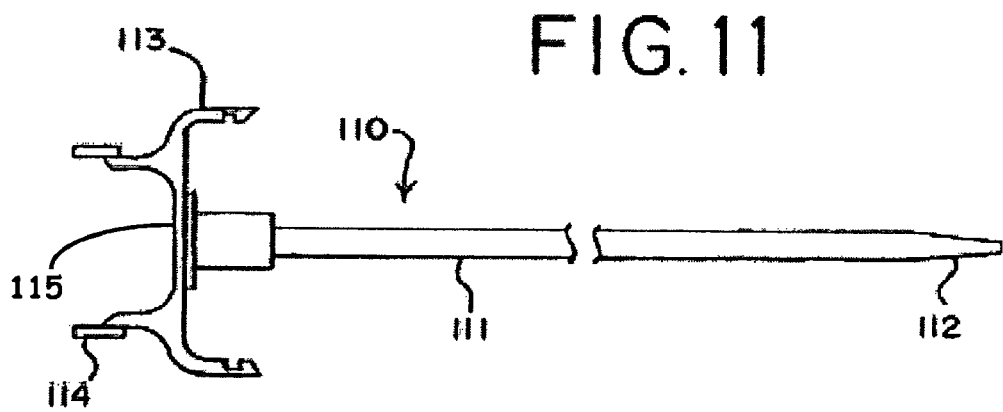
FIG. 11 depicts an obturator for use with a deflectable tip access sheath.

An obturator is useful in deploying an access sheath into a patient. An obturator useful for a deflectable tip access sheath is depicted in FIG. 11. The obturator occupies a lumen of the sheath, preventing its collapse during deployment of the access sheath. Alternatively, the obturator may be used after deployment in order to expand the lumen. The obturator extends from the proximal portion 115 of the access sheath, through the elongated portion, and also preferably through the distal portion as well. Obturator 110 includes a main shaft 111, a distal tip 112, and a proximal portion 115 with connectors 113. Distal tip 112 may be tapered as shown for easier introduction. The proximal portion 115 preferably includes an engaging portion or connectors 113 for clipping or attaching to a proximal portion of the access sheath. The proximal portion 115 may also include release portions 114 for releasing the connecting portions 113. The proximal portion 115 may also include an optional connector, including but not limited to, a luer lock adapter.

Another embodiment of a deflectable tip access sheath is shown in cross-section in FIG. 2. Deflectable-tip access sheath 20 includes a main lumen 22, an auxiliary lumen 23, three lumens 24 for deflector wires, and is covered with hydrophilic coating 21. In this embodiment, the lumens for the deflector wires are spaced at 90° around the periphery of the sheath. Other embodiments may space three deflector lumens and their wires at 120°, while still other embodiments may use a greater or fewer number of deflector wires.

Another embodiment of an insert useful with a deflectable tip access sheath is depicted in FIG. 3a. Insert 25 includes a connecting portion 26 for locking to the proximal portion of the access sheath, the insert operated by finger-operating portions 27. Insert 25 includes an interface 28 and a connector 29. Connector 29 may be a fluid connector, such as for irrigation or drainage from an operating site. Alternately, connector 29 may be a connector for a surgical instrument. Interface 28 may include inner and outer sealing surfaces so that a diagnostic or therapeutic device may be inserted through interface 28. FIG. 3b depicts a partial cross section of a proximal portion of the access sheath for mating with insert 25. Proximal portion 31 includes an outer lip 33 and a gap 32 that interface with the matching portions of insert 25. Proximal portion 31 also includes a lumen 34.

Other embodiments may use inserts with a different configuration. For example, in FIG. 4, insert 40 includes locking portions 41, 43 and an operating portion 42 for slightly spreading locking portions 41, 43 for engagement with the mating portion of an access sheath. In this embodiment, proximal connector 44 may be a connector for a surgical instrument. Distal connector 45 may be a gel-pack type septum or may be a mechanical connector.

FIG. 5 depicts another insert 50 used with a deflectable tip access sheath. The insert includes locking portion 51 and finger-operating portions 52, the insert includes a seal 53 and three proximal connectors 54a, 54c, and 54e. The distal portions 54b, 54f, of the connectors extend through seal 53. One or more of the distal portions of the connectors may extend to the distal portion of the access sheath, for one or more purposes. For instance, proximal connector 54a may connect to a source of irrigation fluid, and distal connector 54b may extend distally to deliver the irrigation fluid to a desired location near a visualization system and an operating site. Distal portion 54d may only extend to within seal 53. In other embodiments, one or more lumens may extend distally through the seal, and in other embodiments, one or more lumens may only extend into the seal.

Proximal connector 54a may be integrally connected with distal connector 54b; for instance, they may have been molded together as a single connector. Distal connector 54b may be placed near the operating field to gather excess irrigation fluid, while proximal connector 54a may be connected to a source of vacuum or partial pressure for gathering the irrigation fluid. It is not necessary that the distal and proximal connectors be integrally connected, as by molding. Instead, one may be a male and another may be a female connector, as with Luer lock connectors, threaded connectors, or snap-fit connectors. Portions of the proximal or distal connectors may extend through the seal 53. In other embodiments, seal 53 is omitted and one or more tubes and lumens may extend through the access sheath to the distal end of the access sheath. For instance, proximal connector 54c may be integrally connected to distal connector 54d, but distal connector 54d may extend only to seal 53, for use, e.g., by a syringe.

Another embodiment may use a plurality of septa, rather than connectors, as part of the deflectable tip access sheath. FIG. 6 depicts interface 60 which may be used as a portion of an insert, as described above. The interface may include a main or larger lumen 61, which may have a liner 61a. As also discussed above, liner 61a may be a hollow spring coil, or it may be a hollow spring coil with an inner polymeric liner. Alternatively, liner 61a may be replaced with a sealing surface. Interface 60 may include one or more lumens 62 for deflector wires, and may also include septa 63, 64 for admission of needles or other sharp, relatively narrow objects. The septa may be made from a sealing material, such as a relatively soft, compliant silicone, or they may be made from other suitable materials, such a gel-pack.

In embodiments of the invention, a deflectable tip access sheath is made by assembling and molding a number of parts. FIGS. 7 and 8 depict processes for making a deflectable tip access sheath. FIG. 7 is a flowchart depicting a process for making a wound coil with an inner polymeric liner. The wound coil with liner may then be used to form a lumen in the process for making an access sheath with a deflectable tip as depicted in FIG. 8.

The process of forming a wound coil with an inner liner includes a step of providing 71 an inner tube, preferably of PTFE or other smooth, relatively friction-free polymer liner. The process also includes providing a preferably stainless steel wire coil 72 having a plurality of turns and an inner diameter less than the outer diameter of the inner polymeric tube. The process then includes winding 73 the coil around the inner tube such that the inner tube is held in compression by the outer tube. The coil spring and inner tube define a lumen for the deflectable tip access sheath. One coil or a plurality of coils may be made for later assembly.

Alternatively, one may purchase coils from a vendor that makes stainless wire into small diameter coils. One such vendor is Star Guide, Denver, Colo., USA. One may assemble to the coiled spring an inner or an outer liner as desired. Vendors may also furnish the coils coated with the desired material. The coils are assembled together by molding a plastic around them, by dipping the coils in plastic, by spraying a coating onto the coils, or by using heat-shrink tubing to apply a polymeric lining inside or outside the coils.

The deflectable tip access sheath is then assembled, as shown in the process of FIG. 8. The coils made by the above-described process are provided 81. A deflectable tip access sheath is then molded 82 from urethane, silicone, or other strong, flexible, medically-acceptable material. A distal end of at least one deflector wire is then connected 83 to a distal portion of the access sheath. This step may be accomplished by molding the distal end of the deflector wire to the distal portion of the access sheath in the previous step. The molding preferably includes forming 84 an interface in a proximal portion of the access sheath. This step may include molding in a connector 85, forming or machining a connector or sealing surface, or any of a number of forming or assembly processes that will result in at least one interface or connector in a proximal portion of the access sheath. Finally, the process includes forming 86 an insert for detachably mounting to the proximal portion of the access sheath.

In one embodiment, the coils and connectors or interfaces may be assembled by molding them together, by joining them adhesively, or by another attachment process. In another embodiment, a proximal portion of the access sheath, such as a funnel, may be overmolded onto the assembled coils and connector, as by insert molding or other suitable molding or attaching process. The molding may be accomplished by an injection molding process, a transfer molding process, or a compression molding process. Other molding processes may also be used to connect the coils and connector to a funnel or proximal portion of the access sheath.

Figure 10:
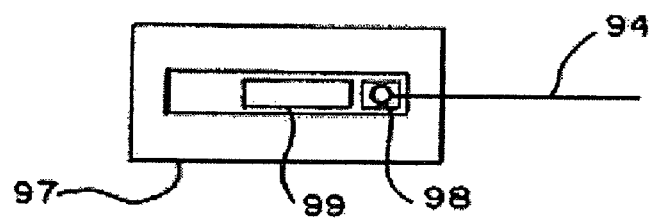

In addition to the access sheath, a handle is used to control the one or more deflector wires that control the deflectable tip access sheath. A thumb ring or pin vise may be used to individually control each wire. However, in embodiments using two or more wires, it is desirable to use a handle to control the wires directly. The handle is preferably secured to the proximal end of the access sheath, as shown in FIG. 1. In one embodiment, the handle may be removable from the access sheath; in another embodiment, the handle may be molded to the access sheath. An example of a handle suitable for a deflector tip access sheath with multiple deflector wires is depicted in FIGS. 9-10.

A deflector tip access sheath 90 has a proximal portion 91, a primary lumen 95, four auxiliary lumens 96 and four deflector wire lumens 93, each shown with a terminating deflector wire 94. A control handle/cap 92 mounts to the proximal portion through connectors 91a, 92a. The cap includes slide locks 97, one slide lock 97 for each deflector wire 94. A deflector wire 94 is secured to the slide lock 97 with a tabbed screw 98, the tab large enough for ease of finger control by the surgeon. The tabbed screw translates distally and proximally in slide 99 as desired by the surgeon, to deflect the tip of the access sheath the desired amount in the desired direction. The slide locks are secure in their position and do not move until the surgeon releases the lock to straighten the tip or to readjust its deflection.

Applications of a Deflectable-Tip Access Sheath

There are many possible applications for a deflectable tip access sheath. One possibility is in the removal of kidney stones from a urinary tract of a patient. In one situation, a patient may have a large kidney stone in a kidney which will not pass through a ureter. A deflectable tip access sheath may have a primary or working lumen ranging from about 6 Fr. to 14 Fr. In addition to at least one additional lumen for at least one deflector wire, the sheath may have an additional lumen with a diameter of about 3 Fr. for optics (about 0.040 inches). The sheath may be placed into the urinary tract by first inserting a guide wire and using an obturator with a central lumen to follow the guide wire into the ureter and kidney of the patient.

The guide wire may then be removed. Using the deflectable tip, the surgeon may locate the kidney stone with the optics portion of the access sheath, and may then wish to use a fiberoptic laser in the primary lumen of the access sheath. There may be sufficient room in the primary lumen of the access sheath for more than single instrument. For instance, there may be sufficient room for a fiberoptic laser to fragment the stone, irrigation for optics and rinsing stone fragments, and a retrieval basket to retrieve the fragments. One such retrieval basket is a 4-wire NCircle® retrieval basket with a 2.4 Fr. PTFE coated polyimide sheath, sold by Cook Urological Inc., Spencer, Ind. Optionally, additional lumens may exist in the access sheath to allow for individual instrument passage, irrigation, and so forth.

In other embodiments, an additional lumen in the access sheath may be used for the fiberoptic laser, while the primary lumen may be used for the irrigation channel and the retrieval basket. In another embodiment, an additional lumen may be used for a retrieval basket, while the primary lumen may be used for the fiberoptic laser and for an irrigation system. The additional lumen gives an additional degree of freedom to the surgeon. There may also be an advantage in simply the spacing or location of the lumens in the access sheath as placed in the patient that makes the additional lumen or lumens desirable for the surgeon. In embodiments with two additional lumens, one may be used as a source of irrigation fluid from one connector, while the other may be connected to a source of vacuum, and used to evacuate irrigation fluid from the operating field.

Embodiments of the invention are not limited to instruments for ureteral procedures. Similar embodiments may be designed for exploration of the common bile duct or other body passages. A deflectable-tip access sheath may be introduced into the abdominal cavity and if necessary, dilation may take place with a balloon angioplasty catheter. A 5.0 Fr. Accent® balloon angioplasty catheter with an 8 mm balloon, available from Cook Incorporated, Bloomington, Ind., may be inserted into the principal channel of the access sheath. The angioplasty catheter may be used to dilate the cystic or common duct, or both. An NCircle® retrieval basket may be inserted through an additional lumen in the access sheath in order to retrieve bile stones if they are sufficiently small. If the bile stones must be fragmented, the additional lumen may be used sequentially for a fiberoptic laser and then for a retrieval basket to gather the stone fragments. The deflectable tip and the additional lumen save time for this procedure and allow the surgeon another degree of freedom in the operating room. This is accomplished with minimal trauma to the patient's tissues.

Another application for a deflectable tip access sheath is for vascular access. One possible application may be for contralateral access to the iliac artery after an initial wire guide position is established. A smaller lumen of the deflectable-tip access sheath may be inserted down the wire guide. This allows direct positioning of the sheath and a dilator, if desired. Once in position, the dilator may be used for vascular access. A Luer lock connector for the additional lumen may be connected to a valve and used for additional vascular access. For instance, instead of depending only on a single lumen for dilation and access, the valve and connector may be used for sampling, aspiration, or for the delivery of medications or marking fluids.

Another application is gastrointestinal access. A deflectable-tip access sheath may be placed as part of a catheter system for access to the stomach and intestinal tract of a patient. The access sheath may be placed by first using a wire guide and inserting the wire guide through one of the lumens of the access sheath. The wire guide may be withdrawn, if desired, and the wire guide lumen may then be used, for instance, for aspiration of gastric contents in the stomach while a larger lumen is used for feeding of the jejunum.

Other urological applications may allow direct percutaneous nephrostomy access (nephroscopy) and direct bladder access (cystoscopy). The working sheath may be used to pass a variety of diagnostic and therapeutic surgical instruments.

Forming Lumens from Coils

The sheath desirably includes spring coils to form the lumens. As shown in U.S. Pat. Nos. 5,380,304 and 5,700,253, assigned to the assignee of the present application, which patents are hereby incorporated by reference in their entirety, coils are formed by taking thin metal wire, preferably stainless steel, and wrapping the wire into a coil. Round wire or flat wire may be used. In one embodiment, 304 stainless steel flat wire measuring about 0.004 inches (0.10 mm)×0.012 (0.30 mm) inches is wrapped into a tight coil having an outer diameter of about 0.164 inches (4.17 mm) and an inner diameter of about 0.156 inches (3.96 mm). A polymer coating, such as a coating or tube made from Teflon®, PTFE, or other fluoropolymer, is applied to the inner diameter. The coating may be applied at any convenient time during the process. Other coatings may be used.

One or more additional lumens may be formed in the sheath by also using metal wire to form a smaller wire coil. For instance, round stainless steel wire with a diameter of about 0.00075 inches (0.02 mm) may be used to wrap a coil with an outer diameter of about 0.040 inches (1.02 mm) and an inner diameter of about 0.0385 inches (0.98 mm). In addition to stainless steel, other medically acceptable materials may also be used, such as nitinol, tungsten, platinum, MP35N, or combinations of metals, such as clad alloys. One example of a clad alloy is MP35N/silver.

In addition to metallic coils, other reinforcements may be used for the lumens in the access sheath. As an example, braided wire may be formed into a coil and then coated as described above. A coil may also be formed from a relatively stiff plastic or polymeric material, such as acetal, polyetheretherketone (PEEK), polyphenylene sulfide (PPS), nylon, ABS, or other suitable polymer. The polymer may include reinforcement, such as glass, carbon or metallic fibers or filaments. The reinforcement may be unidirectional, braided, or woven. Such reinforced polymeric or plastic liners preferably have a smooth skin-effect inner surface for ease of passage of instruments or devices.

Of course, the lumen need not be lined, but may instead be formed by using a removable mandrel to "reserve space" in the sheath during formation of the elongated portion, and then removing the mandrel at some point after formation of the elongated portion. Thus, a mandrel made from PTFE, Teflon®, or other slick, non-binding material may be used. Alternately, or in addition, a mold release compound may be used to coat a mandrel. The compound will preferably not volatilize during molding and should not prevent curing consolidation of the thermoplastic or thermoset material that forms a considerable part of the elongated portion. Mold release compounds are available from a number of manufacturers, including the McLube series of compounds available from McGee Industries, Inc., of Aston, Pa.

Assembling the Coils into a Sheath

Once the coils are formed, and desirably coated, they are assembled into a sheath. This assembly process desirably takes place in at least two steps. There is typically, but not necessarily, a larger coil for the primary lumen and one or smaller coils for the other lumens. The larger coil will be used for the primary lumen. The smaller coil(s) may be used for the deflector wires and for lumens for irrigation, optics, guide wire insertion, and the like. The smaller coils may require a connector in order to function effectively. Thus, if irrigation fluid is to be introduced through an auxiliary lumen, a connector to a source of irrigation fluid is needed. If evacuation of fluid or irrigation is desired, a connector suitable for a vacuum connection may be desirable. Even if the additional lumen is used only for a guide wire, it will be preferable to terminate the auxiliary lumen in such a manner that operating room personnel have access to the lumen. Thus, the proximal portion of the sheath, the handle, desirably has an interface or termination point for the additional lumen that may be viewed and accessed by operating room personnel. The above description is not meant to be limiting, and only a few of the possible embodiments have been described. For instance, emphasis has been placed on the use of coils to achieve flexibility in the access sheaths. However, it is also possible to form a lumen with tubing rather than a coiled spring. The tubing may be rendered flexible by a series of cuts, such as spiral cuts in one or more regions of the tubing for flexibility in selective regions. The tubing may be cut or slit, for example, by laser cutting, as described in application Ser. No. 10/617,580, now U.S. Published Application No. 2004/0054377, assigned to the assignee of the present application. Processes for making an access sheath are also described in application Ser. No. 11/089,063, now U.S. Published Application No. 2005/0222581, also assigned to the assignee of the present application. These two applications are hereby incorporated by reference in their entirety as though they were reproduced word for word and figure for figure on the pages of this patent.

The coils or tubing that define lumens in the deflectable-tip access sheath are preferably lined with a smooth polymer, in order to minimize friction as objects, such as retrieval baskets or wire guides, are passed through the lumens. While fluoropolymers as described above make excellent liners, other materials may also be used, such as urethanes and olefins. The liners themselves may also be coated, if the application requires, with lubricious or hydrophilic coatings.

An interface or connector will be very helpful in order for operating room personnel to efficiently use the at least one additional lumen in the access sheath. Even if the interface is only a chamfered or beveled surface on the top of the proximal portion, it will help operating room personnel use the additional lumen. The lumen is preferably a connector, such as a Luer lock, or other "universal" connector that is easily usable to connect to syringes, sources of vacuum, fluid plumbing devices such as valves, or other medical devices. While a connector is preferred, any interface that assists operating room personnel in using the one or more additional lumens is intended.

The elongated portion of the deflectable tip access sheath is actually a relative small fraction of the material used in the sheath, because much of the volume is taken up by the tubing or coils that define the lumens. The elongated portion may be made from one or more layers of heat-shrink tubing, such as urethane or PTFE heat-shrink tubing, wrapped around the coils or tubing. Other materials, such as nylons or olefins, may also be used so long as they are medically acceptable. Films or thin strips of material may also be wrapped or formed around the tubing or coils to form the elongated portion, rather than merely heating heat-shrink tubing. The assembled coils or tubes and polymeric materials may then be placed into a mold or form and the polymeric material consolidated and molded. This is another way to integrally-connect a connector.

The deflectable tip access sheath is desirably assembled in stages, as described above, or it may be molded at once. For instance, coils and liners defining the lumens may be prepared and wrapped with polymeric materials for consolidation into an integrated elongated portion. A connector or interface is desirably added to at least one coil defining a lumen, preferably a smaller coil, at this stage. The connector or interface may be adhesively bonded to the coil, or may be mechanically connected or fitted to the coil. A subassembly of the elongated portion and the connector may then be insert molded to a proximal portion. This may be accomplished by any number of molding techniques.

Alternatively, the entire sheath may be insert molded in a single step by placing spring coils or tubing into a mold, and then injecting plastic or compressing or transferring a polymeric material to define the access sheath and its proximal portion, including an interface or connector for the additional lumen. A single-step method may not be desirable because of the elongated nature of the sheath and the expense of a tool large enough to accommodate what may be a very long sheath, from 30 up to 250 cm long. Access sheaths for urology may be about 75 cm long. Also adding to tooling expense is the complexity of a proximal portion that may include a flared funnel, or a funnel portion, and an additional connector in either case. The deflectable tip access sheath may be made by this method. However, a two-step process as described above, will be more effective in controlling the process and the cost, and will likely result in a more uniform product.

Figure 17:
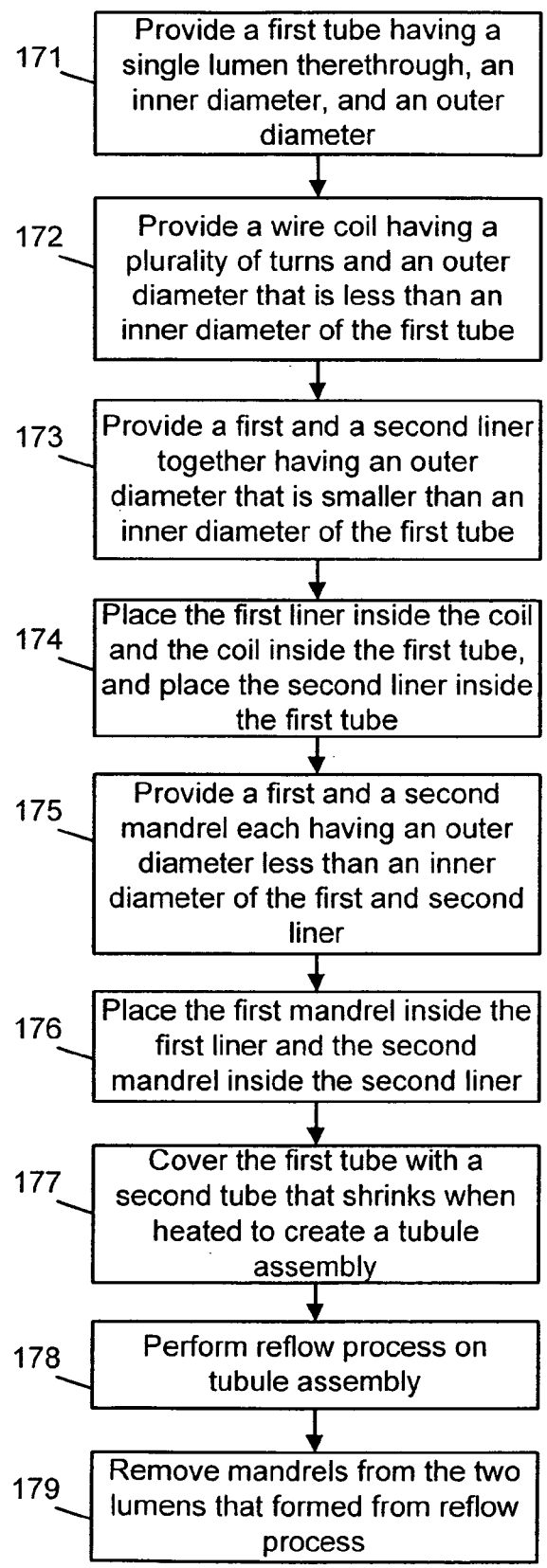
FIG. 17 is a flowchart depicting a method of manufacturing a sheath.

An alternative method of making a sheath is also depicted in FIG. 17. FIG. 17 provides a method of making a multiple lumen sheath from either a single lumen or multi-lumen extrusion using a reflow melting process. In particular, a single or multi-lumen tube is provided, as are a coil wire having a plurality of turns and a specific number of liners needed for the final sheath. For example, if a sheath having two lumens is desired, a single lumen tube is provided 171, as are a coil wire having a plurality of turns 172 and a specific number of liners needed for the final sheath 173. The combined outer diameter of the liners is less than an inner diameter of the first tube 173. The first liner is placed inside the coil and the coil is placed inside the first tube 174. The second liner is placed directly into the first tube 174. A first and second mandrel having outer diameters that are less than the inner diameters of the liners 175 are placed inside each of the liners 176. The first tube is then covered with a heat shrink tube to create a tubule assembly 177. The reflow process 178 is then performed on the tubule assembly. The reflow process consists of heating the tubule assembly above the melting point of the polymer of the single or multi-lumen tube and the activation temperature of the heat shrink tube and squeezing the material into the desired configuration. Baking time is dependent upon the size and configuration of the desired sheath. After cooling, the mandrels are then removed leaving the desired number of lumens inside the first tube that were created using the reflow process 179. Additional lumens can be created by using additional mandrels during the reflow process. Moreover, sheaths extruded with multiple lumens can also benefit from this process by having lumens shrunk to an inserted mandrel size by using the reflow process. Additionally, although a coil is preferred in order to create flexibility and liners are preferred to make the lumens smoother, neither is required.

Figure 12:
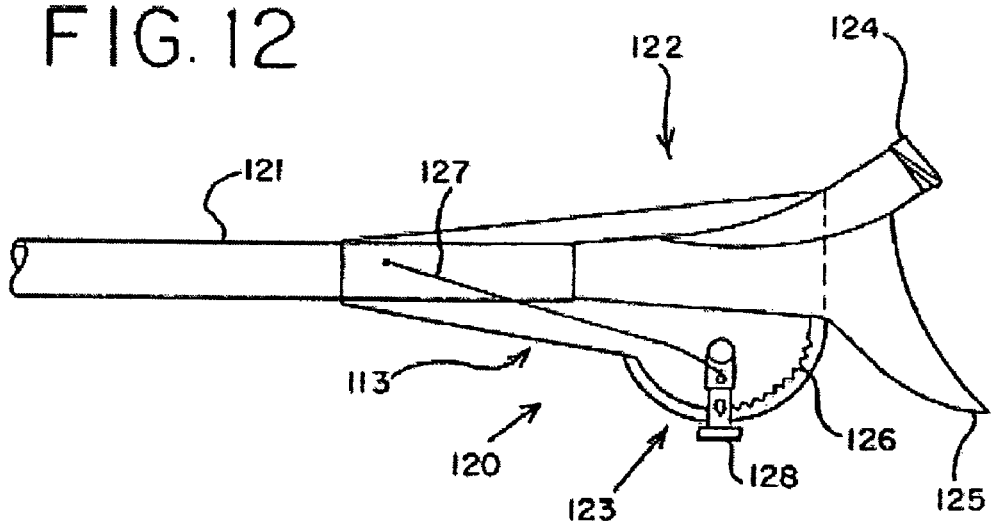
FIGS. 12-14 depict a deflectable tip access sheath with handle components.
Figure 13:
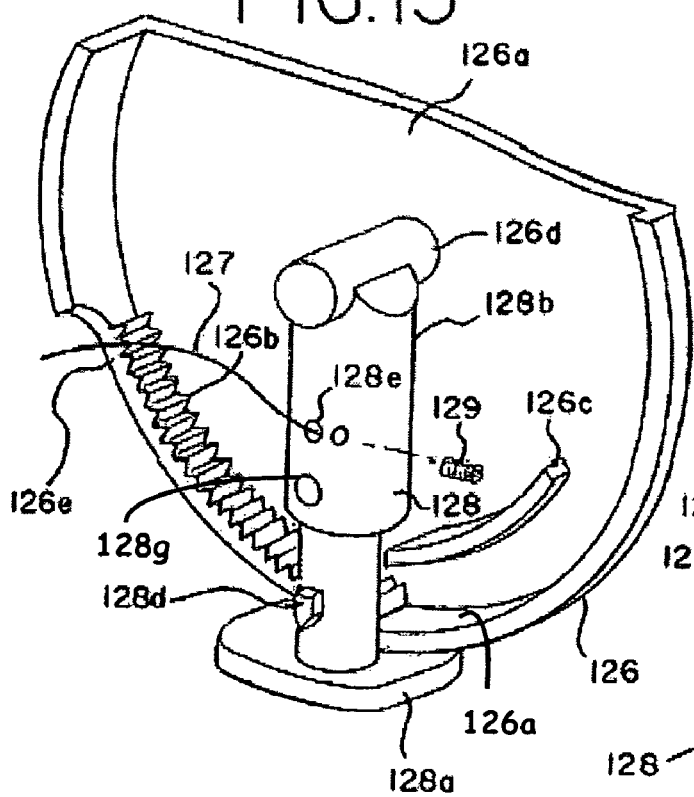
Figure 14:
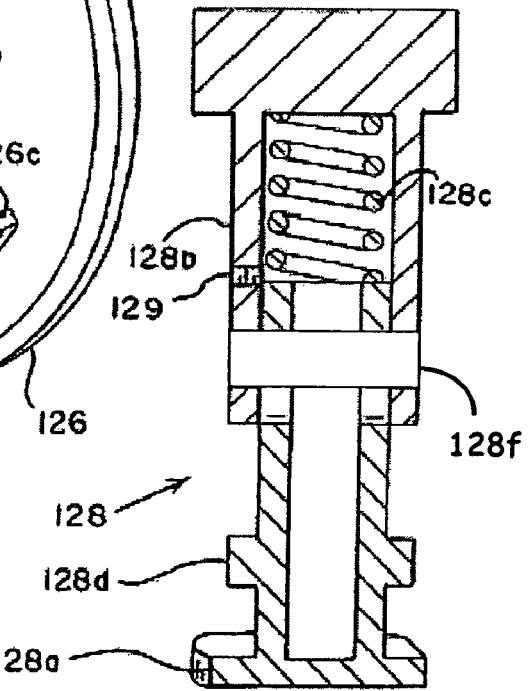

The deflectable tip access sheath preferably has a handle and easy-to-use controls so that the physician or medical professional can readily adjust the position and deflection of the tip. FIGS. 12-14 illustrate one embodiment of controls for a deflection wire and a deflectable tip access sheath. Deflectable tip access sheath 120 includes a deflectable tip distal portion (not shown), a middle flexible portion 121, and a proximal portion 122. The proximal portion includes a control portion 123, a connector 124, and an elongated funnel portion 125. As also shown in FIG. 12, there is at least one deflection control wire 127, for connection to an actuator 128 portion that interfaces with a retainer 126.

Retainer 126 is preferably molded into the proximal portion of the deflectable tip access sheath, or otherwise assembled in place. Retainer 126 has a base portion 126a, a preferably curved rack 126b of teeth, and a stop 126c. The base portion also has a pivot point or pin 126d and a guide 126e for the pivot pin. One aperture is for access for deflection wire 127. The other aperture is for assembly of actuator 128. Actuator 128 includes a proximal portion 128a for interfacing with the hand or thumb of a user, and a distal portion 128b which mounts on pivot point 126d. Spring 128c allows the user to depress proximal portion 128a, pivoting actuator 128 on pivot point or pin 126d, moving tooth 128d and its position in rack 126b. Pin 128f interfaces with orifice 128g so that proximal portion 128a does not separate from distal portion 128b by the force of spring 128c. Deflector wire 127 is routed through orifice 128e and is retained by retaining screw 129 in a transverse orifice. This is one convenient method for adjusting incrementally a position of the deflector wire 127 and thus the position of the deflectable tip of the access sheath. More than one deflector wire and more than one proximal control may be used.

Figure 15:
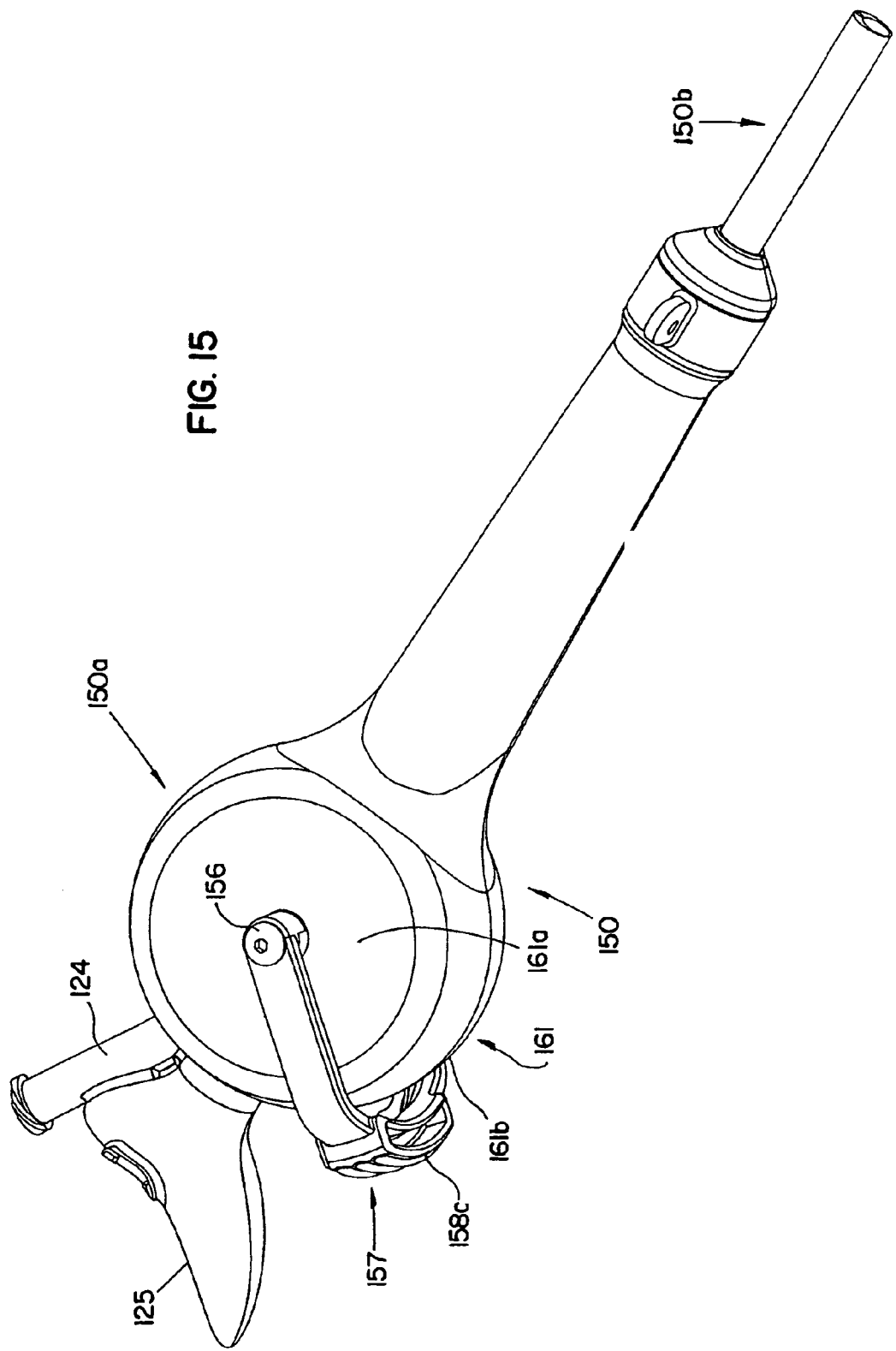
FIGS. 15-16 depict an alternate embodiment of a deflectable tip access sheath with handle components.
Figure 16:
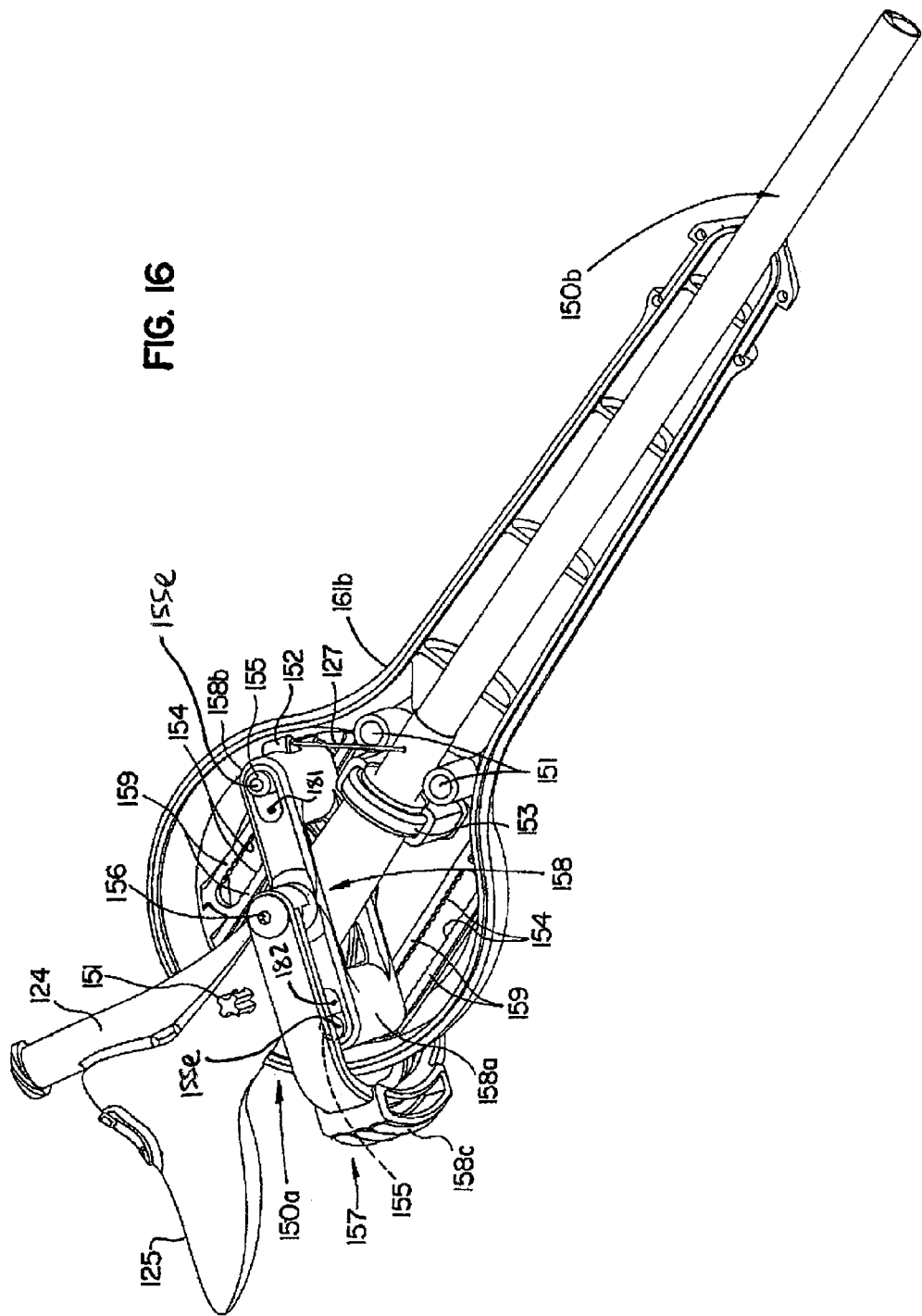

FIGS. 15-16 depict an alternate embodiment of a deflectable tip access sheath 150. Deflectable tip access sheath 150 includes a deflectable tip distal portion (not shown), a middle flexible portion 150b, and a proximal portion 150a. Proximal portion 150a includes a control portion 157 that is covered by housing 161 having two portions 161a, 161b held together via a plurality of snap-fits 151. Alternatively, housing portions 161a, 161b can be held together via other means including, but not limited to, glue, screws, and other types of fasteners. Stabilizer 153 is a recessed groove in housing 161 to help maintain the position of the proximal portion 150a relative to that of the middle flexible portion 150b.

Control portion 157 includes a connector 124, an elongated funnel portion 125, and a deflection control wire 127 that is connected to actuator assembly 158. In particular, deflection control wire 127 is disposed partially within middle flexible portion 150b and is directed into wire cannula (not shown) through cylindrical portion 152 located at distal portion 158b of actuator assembly 158. It is preferred that the cannula (not shown) that is attached to deflection control wire 127 not be attached to actuator assembly 158. Deflection control wire 127 is partially disposed through cylindrical portion 152 and then through cannula (not shown). Deflection control wire 127 is secured in the cannula using an arch weld (not shown). The other end of deflection control wire 127 is attached to the distal end of the device (not shown). Alternatively, deflection control wire 127 may be secured via other means including, but not limited to, a set screw (not shown).

At proximal portion 158a of actuator assembly 158 is actuator 158c that is able to pivot around control portion 157 via pivot point 156. As shown, pivot point 156 is secured with a screw; control portion 157 and actuator 158 pivot simultaneously with housing 161; however, other pivoting means are contemplated. As actuator 158c is pushed in the direction of middle flexible portion 150b, retention points 155 slide along retainers 159. As shown in FIG. 16, retention points include slots 181, 182 that receive pins 155e therethrough to allow the retention points 155 to slide along the respective retainer 159. As retention points 155 slide along retainers 159, deflection control wire 127 is pulled causing distal portion of deflectable access sheath (not shown) to deflect. Optional detents (teeth) 154 of retainers 159 help to modulate the movement of actuator assembly 158.

Housing 161 may be optionally molded to have a form such that actuator assembly 158 is unable to be pushed or pulled in a direction that would risk breaking the device. Additionally, optional stops (as depicted in FIG. 13) could also be added to the device to prevent over-stressing the actuator assembly 158 and the deflection control wire 127.

One or more additional deflection control wires could optionally be added to deflectable access sheath to provide for multi-directional or multi-planar deflection of the sheath. For example, an additional wire cannula could be placed at the proximal portion 158a of actuator assembly 158 wherein an additional deflection control wire could be attached. In addition, a tool, including, but not limited to, a retrieval basket (not shown) can be movably disposed within middle flexible portion 150b It is intended that the foregoing detailed description be regarded as illustrative rather than limiting, and that it be understood that it is the following claims, including all equivalents, that are intended to define the spirit and scope of this invention.

What is claimed:

1. An access sheath, comprising:
   a proximal portion comprising a control handle disposed within a housing having a first track;
   a distal portion adapted for bending at an angle;
   an elongated portion extending from the proximal portion through the distal portion, the elongated portion comprising a working lumen and two additional lumens, one of said lumens adapted to receive an optical system; and
   at least one deflector filament in at least one of said additional lumens, the at least one deflector filament operatively coupled to the distal portion and extending to the proximal portion, deflector filament being mechanically coupled to the control handle, wherein the control handle is rotatably mounted within the housing such that rotation of the control handle urges linear movement of the deflector filament within the at least one of said additional lumens,
   the control handle comprises a rotatable operative portion that extends out of the housing and a second portion that comprises an actuator assembly that is fixed to the deflector filament, the actuator assembly comprises a first retention point that includes a first pin that is slidable within the first track defined within the housing, and wherein the first retention point includes a first slot that allows for relative linear movement of the first pin within the first retention point, and wherein torque is transferred from the operative portion to the second portion through a pivot point connecting the operative portion and the second portion to rotate together.

2. The access sheath of claim 1, wherein an obturator is attachable to the housing.

3. The access sheath of claim 2, wherein the housing includes a portion is shaped like a funnel.

4. The access sheath of claim 1, wherein the control handle is adapted for incremental movement.

5. The access sheath of claim 4, further comprising at least two deflector wires;
 wherein the deflector wires are in communication with the control handle.

6. The access sheath of claim 1, wherein the second portion comprises a second retention point that supports a second pin that is slidable within a second track in the housing.

7. The access sheath of claim 6, wherein the second retention point includes a second slot that allows for relative motion of the second pin within the second retention point.

8. The access sheath of claim 1, further comprising at least one connector mounted to the proximal end of the access sheath.

9. The access sheath of claim 1, wherein at least one of the lumens is formed on the inside of a coiled wire.

10. The access sheath of claim 1, further comprising an insert for mounting to the proximal end of the access sheath, the insert comprising a connector and a mating interface.

11. The access sheath of claim 1, further comprising an insert adapted for removably clipping onto the proximal end of the access sheath.

12. The access sheath of claim 1 further comprising at least one additional lumen around the deflector wire.

13. The access sheath of claim 1, further comprising a coil around one of the lumens, and further comprising a coating on an inside of the coil.

14. The access sheath of claim 1, wherein the elongated portion further comprises a coil in compression around an inner plastic tube, the coil and plastic tube around one of the lumens.

15. The access sheath of claim 1, wherein the distal portion is adapted for bending at an angle of at least 180°.

16. The access sheath of claim 1, further comprising a removable obturator configured to be selectively inserted through the elongated portion and extend through and out of the distal portion.

17. An access sheath, comprising:
 an elongated access sheath extending from a proximal portion to a distal portion, the proximal portion having at least one connector and an interface;
 at least one coil embedded within the access sheath, the coil reinforcing at least a portion of a lumen extending from the proximal portion to the distal portion;
 at least one additional lumen extending from the proximal portion to the distal portion and adapted to receive an optical system or a portion of an irrigation system; and
 at least one deflector filament operatively coupled to the distal portion and extending through the access sheath, the deflector filament and access sheath adapted for bending the distal portion of the access sheath at an angle,
 wherein the interface includes a housing with a first track and a control handle that is mechanically coupled to the deflector filament, the control handle is rotatably mounted within the housing upon a pivot point, wherein the control handle is configured to cause linear movement of the deflector filament within the access sheath with rotation of the control handle,
 the control handle includes a rotatable operative portion that extends out of the housing and a second portion that comprises an actuator assembly fixed to the deflector filament, and the actuator assembly comprises a first retention point that includes a first in that is slidable within the first track defined within the housing, wherein the first retention point includes a first slot that allows for relative linear motion of the first pin within the first retention point, wherein torque is transferred from the operative portion to the second portion through the pivot point which connects the operative portion and the second portion to rotate together.

18. The access sheath of claim 17, wherein the second portion comprises a second retention point that supports a second pin that is slidable within a second track in the housing.

19. The access sheath of claim 18, wherein the second retention point includes a second slot that allows for relative motion of the second pin within the second retention point.

20. The access sheath of claim 17, wherein the distal portion is adapted for bending at an angle of at least 180°.

21. The access sheath of claim 17, wherein the at least one coil is selected from the group consisting of a coiled wire, a braided wire, a polymeric coil and a filament-reinforced polymeric coil.

22. The access sheath of claim 17, further comprising an insert for mounting to the proximal portion of the access sheath, the insert further comprising a mating interface.

23. The access sheath of claim 17, further comprising an insert for mounting to the proximal portion of the access sheath, the insert further comprising a mating interface and a septum.

24. The access sheath of claim 17, further comprising an insert for mounting to the proximal portion of the access sheath, the insert further comprising a mating interface and at least one connector.

25. The access sheath of claim 17, further comprising a removable obturator configured to be selectively inserted through the access sheath through and out of the distal portion.

26. The access sheath of claim 17, further comprising a polymeric lining between the lumen and the coil.

* * * * *

UNITED STATES PATENT AND TRADEMARK OFFICE
CERTIFICATE OF CORRECTION

PATENT NO. : 7,803,130 B2 Page 1 of 1
APPLICATION NO. : 11/649683
DATED : September 28, 2010
INVENTOR(S) : Walter N. Ryan et al.

It is certified that error appears in the above-identified patent and that said Letters Patent is hereby corrected as shown below:

On the Title Page

Item (73), after "Vance Products Inc.," insert
--d/b/a Cook Urological Incorporated--.

Signed and Sealed this

Twenty-first Day of December, 2010

David J. Kappos
*Director of the United States Patent and Trademark Office*